United States Patent [19]

Bundy

[11] 4,154,764
[45] May 15, 1979

[54] 2-DECARBOXY-2-ALKYLCARBONYL-PGD COMPOUNDS

[75] Inventor: Gordon L. Bundy, Portage, Mich.

[73] Assignee: The Upjohn Company, Kalamazoo, Mich.

[21] Appl. No.: 925,257

[22] Filed: Jul. 17, 1978

Related U.S. Application Data

[62] Division of Ser. No. 888,695, Mar. 21, 1978, Pat. No. 4,123,463.

[51] Int. Cl.$^2$ .............................................. C07C 177/00
[52] U.S. Cl. ............................. 260/586 R; 260/590 C
[58] Field of Search ....................... 260/586 R, 590 C

[56] References Cited

U.S. PATENT DOCUMENTS 3,931,296  1/1976  Hayashi et al. ...................... 560/121
3,953,435  4/1976  Hayashi et al. ........................ 54/426
4,066,751  1/1978  Hayashi et al. ...................... 560/121

OTHER PUBLICATIONS

Derwent CPI Farmdoc 93049/50.
Derwent Farmdoc CPI No. 35953x.
Derwent Farmdoc CPI No. 94924x.

Primary Examiner—Gerald A. Schwartz
Attorney, Agent, or Firm—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

51 Claims, No Drawings

2-DECARBOXY-2-ALKYLCARBONYL-PGD COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from U.S. Pat. No. 4,123,463.

I claim:

1. A prostaglandin analog of the formula $$D\begin{matrix} CH_2-Z_1-\overset{O}{\underset{\|}{C}}-R_1 \\ Y_1-\underset{\underset{M_1}{\|}}{C}-\underset{\underset{L_1}{\|}}{C}-R_7 \end{matrix}$$

wherein D is (structures shown)

wherein $R_1$ is alkyl of one to 4 carbon atoms, inclusive;

wherein $L_1$ is $$\overset{R_3}{\diagup}\overset{R_4}{\diagdown}, \overset{R_3}{\diagup}\overset{R_4}{\diagdown}, \text{ or}$$

a mixture of $$\overset{R_3}{\diagup}\overset{R_4}{\diagdown}$$

and $$\overset{R_3}{\diagup}\overset{R_4}{\diagdown},$$

wherein $R_3$ and $R_4$ are hydrogen, methyl, or fluoro, being the same or different, with the proviso that one of $R_3$ and $R_4$ is methyl only when the other is hydrogen or methyl;

wherein $M_1$ is $$\overset{R_5}{\diagup}\overset{OH}{\diagdown} \text{ or}$$

$$\overset{R_5}{\diagup}\overset{OH}{\diagdown},$$

wherein $R_5$ is hydrogen or methyl;

wherein $R_7$ is (1) $-(CH_2)_m-CH_3$, (2) $-(CH_2)_n-\text{(phenyl with }(T)_s\text{)}$, or (3) $-O-\text{(phenyl with }(T)_s\text{)}$, wherein h is zero to three, inclusive,
wherein m is one to 5, inclusive, s is zero, one, 2, or 3 and T is chloro, fluoro, trifuloromethyl, alkyl of one to 3 carbon atoms or alkoxy of one to 3 carbon atoms, the various T's being the same or different, with the proviso that not more than two T's are other than alkyl;

wherein $Y_1$ is
(1) trans$-CH=CH-$,
(2) cis$-CH=CH-$,
(3) $-CH_2CH_2-$, or
(4) $-C\equiv C-$; and wherein $Z_1$ is
(1) cis$-CH=CH-CH_2-(CH_2)_g-CH_2-$,
(2) cis$-CH=CH-CH_2-(CH_2)_g-CF_2-$,
(3) cis$-CH_2-CH=CH-(CH_2)_g-CH_2-$,
(4) $-(CH_2)_3-(CH_2)_g-CH_2-$,
(5) $-(CH_2)_3-(CH_2)_g-CF_2-$,
(6) $-CH_2-O-CH_2-(CH_2)_g-CH_2-$,
(7) $-(CH_2)_2-O-(CH_2)_g-CH_2-$,
(8) $-(CH_2)_3-O-(CH_2)_g-$,
(9) $-C\equiv C-CH_2-(CH_2)_g-CH_2-$,
(10) $-CH_2-C\equiv C-(CH_2)_g-CH_2-$, or
(11) trans$-(CH_2)_2-(CH_2)_g-CH=CH-$,
wherein g is one, two, or three.

2. A prostaglandin analog according to claim 1, wherein $R_1$ is methyl.

3. A prostaglandin analog according to claim 2, wherein D is (structure)

4. 2-Decarboxy-2-methylcarbonyl-$8\beta,12\alpha$-PGD$_2$, a prostaglandin analog according to claim 3.

5. A prostaglandin analog according to claim 2, wherein D is (structure)

6. 2-Decarboxy-2-methylcarbonyl-9β,PGD$_2$, a prostaglandin analog according to claim 5.

7. A prostaglandin analog according to claim 2, wherein D is

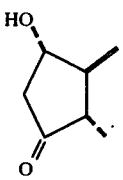

8. 2-Decarboxy-2-methylcarbonyl-8β,9β,12α-PGD$_2$, a prostaglandin analog according to claim 7.

9. A prostaglandin analog according to claim 2, wherein D is

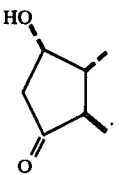

10. A prostaglandin analog according to claim 9, wherein Y$_1$ is cis—CH═CH—.

11. 2-Decarboxy-2-methylcarbonyl-13-cis-PGD$_1$, a prostaglandin analog according to claim 10.

12. A prostaglandin analog according to claim 9, wherein Y$_1$ is —CH$_2$CH$_2$—.

13. 2-Decarboxy-2-methylcarbonyl-13,14-dihydro-PGD$_1$, a prostaglandin analog according to claim 12.

14. A prostaglandin analog according to claim 9, wherein Y$_1$ is —C≡C—.

15. 2-Decarboxy-2-methylcarbonyl-13,14-didehydro-PGD$_1$, a prostaglandin analog according to claim 14.

16. A prostaglandin analog according to claim 9, wherein Y$_1$ is trans—CH═CH—.

17. A prostaglandin analog according to claim 16, wherein R$_7$ is

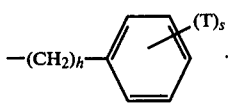

18. 2-Decarboxy-2-methylcarbonyl-17-phenyl-18,19,20-trinor-PGD$_1$, a prostaglandin analog according to claim 17.

19. A prostaglandin analog according to claim 16, wherein R$_7$ is

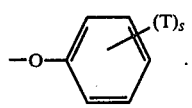

20. 2-Decarboxy-2-methylcarbonyl-16-phenoxy-17,18,19,20-tetranor-PGD$_1$, a prostaglandin analog according to claim 19.

21. A prostaglandin analog according to claim 16, wherein R$_7$ is —(CH$_2$)$_m$—CH$_3$—.

22. A prostaglandin analog according to claim 21, wherein Z$_1$ is cis—CH—CH—CH$_2$—(CH$_2$)$_g$—CF$_2$—.

23. 2-Decarboxy-2-methylcarbonyl-2,2-difluoro-PGD$_1$, a prostaglandin analog according to claim 22.

24. A prostaglandin analog according to claim 21, wherein Z$_1$ is cis—CH$_2$═CH—CH—(CH$_2$)$_g$—CH$_2$—.

25. 2-Decarboxy-2-methylcarbonyl-cis-4,5-didehydro-16,16-dimethyl-PGD$_1$, a prostaglandin analog according to claim 24.

26. A prostaglandin analog according to claim 21, wherein Z$_1$ is —(CH$_2$)$_3$—(CH$_2$)$_g$—CH$_2$—.

27. 2-Decarboxy-2-methylcarbonyl-PGD$_1$, a prostaglandin analog according to claim 26.

28. A prostaglandin analog according to claim 21, wherein Z$_1$ is —(CH$_2$(3—(CH$_2$)$_g$—CF$_2$—.

29. 2-Decarboxy-2-methylcarbonyl-2,2-difluoro-PGD$_1$, a prostaglandin analog according to claim 28.

30. A prostaglandin analog according to claim 21, wherein Z$_1$ is —CH$_2$—O—CH$_2$—(CH$_2$)$_g$—CH$_2$—.

31. 2-Decarboxy-2-methylcarbonyl-5-oxa-PGD$_1$, a prostaglandin analog according to claim 30.

32. A prostaglandin analog according to claim 21, wherein Z$_1$ is —(CH$_2$)$_2$—O—(CH$_2$)$_g$—CH$_2$—.

33. 2-Decarboxy-2-methylcarbonyl-4-oxa-PGD$_1$, a prostaglandin analog according to claim 32.

34. A prostaglandin analog according to claim 21, wherein Z$_1$ is —(CH$_2$)$_3$—O—(CH$_2$)$_g$—.

35. 2-Decarboxy-2-methylcarbonyl-3-oxa-PGD$_1$, a prostaglandin analog according to claim 34.

36. A prostaglandin analog according to claim 21, wherein Z$_1$ is —C≡C—CH$_2$—(CH$_2$)$_g$—CH$_2$—.

37. 2-Decarboxy-2-methylcarbonyl-5,6-didehydro-PGD$_1$, a prostaglandin analog according to claim 36.

38. A prostaglandin analog according to claim 21, wherein Z$_1$ is —CH$_2$—C≡C—(CH$_2$)$_g$—CH$_2$—.

39. 2-Decarboxy-2-methylcarbonyl-4,4,5,5-tetradehydro-PGD$_1$, a prostaglandin analog according to claim 38.

40. A prostaglandin analog according to claim 21, wherein Z$_1$ is trans—(CH$_2$)$_2$—(CH$_2$)$_g$—CH═CH—.

41. 2-Decarboxy-2-methylcarbonyl-trans-2,3-didehydro-PGD$_1$, a prostaglandin analog according to claim 40.

42. A prostaglandin analog according to claim 21, wherein Z$_1$ is cis—CH═CH—CH$_2$—(CH$_2$)$_g$—CH$_2$—.

43. A prostaglandin analog according to claim 42, wherein R$_5$ is methyl.

44. 2-Decarboxy-2-methylcarbonyl-15-methyl-PGD$_1$, a prostaglandin analog according to claim 42.

45. A prostaglandin analog according to claim 42, wherein R$_5$ is hydrogen.

46. A prostaglandin analog according to claim 45, wherein one of R$_3$ and R$_4$ is fluoro.

47. 2-Decarboxy-2-methylcarbonyl-16,16-difluoro-PGD$_1$, a prostaglandin analog according to claim 46.

48. A prostaglandin analog according to claim 45, wherein at least one of R$_3$ and R$_4$ is methyl.

49. 2-Decarboxy-2-methylcarbonyl-16,16-dimethyl-PGD$_1$, a prostaglandin analog according to claim 48.

50. A prostaglandin analog according to claim 45, wherein R$_3$ and R$_4$ are both hydrogen.

51. 2-Decarboxy-2-methylcarbonyl-PGD$_1$, a prostaglandin analog according to claim 50.

* * * * *

UNITED STATES PATENT OFFICE
CERTIFICATE OF CORRECTION

Patent No. 4,154,764                    Dated May 15, 1979

Inventor(s) Gordon L. Bundy

It is certified that error appears in the above-identified patent and that said Letters Patent are hereby corrected as shown below:

Column 2, lines 10-13,

Column 3, lines 5-12,

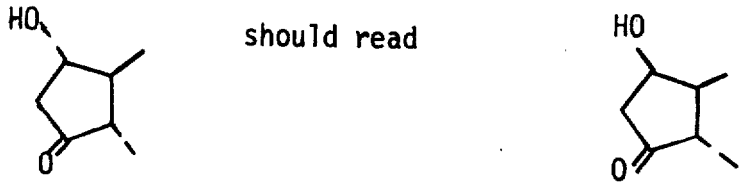

Column 4, line 2, "cis-CH-CH-" should read -- cis-CH=CH- --; lines 4, 33, 49, 55, 59, 62, "PGD$_1$" should read -- PGD$_2$ --; line 15, "-(CH$_2$($_3$" should read -- -(CH$_2$)$_3$ --.

UNITED STATES PATENT OFFICE
CERTIFICATE OF CORRECTION

Patent No. 4,154,764             Dated 15 May 1979

Inventor(s) Gordon L. Bundy

It is certified that error appears in the above-identified patent and that said Letters Patent are hereby corrected as shown below:

Column 4, line 8, "$PGD_1$" should read -- $PGD_2$ --.

Column 4, line 6, "cis-$CH_2$ = CH-CH-$(CH_2)$g-$CH_2$-" should read -- cis-$CH_2$-CH = CH-$(CH_2)$g-$CH_2$- --.

*Signed and Sealed this*

*Twentieth* Day of *November 1979*

[SEAL]

*Attest:*

RUTH C. MASON
*Attesting Officer*

LUTRELLE F. PARKER
*Acting Commissioner of Patents and Trademarks*